United States Patent [19]
Joh et al.

[11] Patent Number: 4,822,352
[45] Date of Patent: Apr. 18, 1989

[54] MEDICAL TUBES WITH POROUS TEXTURED WALLS

[75] Inventors: Yasushi Joh; Noriaki Kaneko, both of Yokohama, Japan

[73] Assignee: Ube Industries, Ltd., Ube, Japan

[21] Appl. No.: 66,849

[22] Filed: Jun. 25, 1987

[30] Foreign Application Priority Data

Aug. 8, 1986 [JP] Japan .................. 61-185165

[51] Int. Cl.$^4$ .............................. A61F 2/06
[52] U.S. Cl. ........................... 623/1; 623/12; 623/66; 128/334 R; 252/321; 264/41; 264/334; 106/122
[58] Field of Search ............. 128/334 C; 252/321; 264/334, 54, 41; 623/1, 11, 12, 66; 106/122; 521/137

[56] References Cited

U.S. PATENT DOCUMENTS

| | | | |
|---|---|---|---|
| 4,071,532 | 1/1978 | Rose | 264/334 |
| 4,173,689 | 11/1979 | Lyman et al. | 623/1 |
| 4,269,713 | 5/1981 | Yamashita | 264/41 |
| 4,355,426 | 10/1982 | MacGregor | 623/1 |
| 4,436,869 | 3/1984 | Zipp et al. | 264/54 |
| 4,661,530 | 4/1987 | Gogolewski et al. | 623/1 |

Primary Examiner—Richard J. Apley
Assistant Examiner—Paul Prebilic
Attorney, Agent, or Firm—Frishauf, Holtz, Goodman & Woodward

[57] ABSTRACT

Disclosed is a medical tube comprising a mono-layer medical tube comprising a high molecular weight compound, wherein the inner texture of a tube wall constituting the tube is porous and no skin layer is present on the inner face of the tube wall.

The porous inner texture of the tube is microscopically spongy and contains cells or voids interconnected by pores. The inner wall of the tube contains concavities which open into the cells or voids and communicates them with any fluid flowing through the tube.

Disclosed is also a process for producing a medical tube, comprising thrusting forward a core rod having a round cross-section and made of a rigid body from a circular orifice to extrude a solution of a high molecular weight compound from a gap slit defined between the orifice and the core rod in such a manner that the solution is spread over the whole surface of the core rod, and leading the core rod in a solidifying medium to solidify the high molecular weight compound around the core rod, followed by taking out the core rod.

The medical tubes of this invention or the medical tubes produced by the present process has excellent compatibility with blood, particularly is suitable for an artificial blood vessel which is required to have excellent long term patency.

3 Claims, 2 Drawing Sheets

MEDICAL TUBES WITH POROUS TEXTURED WALLS

BACKGROUND OF THE INVENTION

This invention relates to a medical tube and a process for producing the same. More particularly, it relates to a medical tube having excellent compatibility with blood, particularly suited for an artificial blood vessel, and a process for producing the same.

Conventionally known process for producing medical tubes comprising thermoplastic high molecular weight compounds may include a process in which a high molecular weight compound is heat-melted, followed by extrusion (hereinafter called a "melt extrusion process"); a process in which a round rod-shaped mold is repeatedly dipped in a polymer solution until a polymer layer of a desired thickness is formed on it (hereinafter called a "dip process"); and a, process in which a solution comprising a high molecular weight compound is extruded from an annular orifice while an inside solidifying solution is extruded from the center of the annular orifice, and the whole is dipped in an outside solidifying solution (Japanese Unexamined Patent Publication No. 188164/1985).

However, any of these process may not obtain medical tubes that can exhibit the compatibility with blood with good reproducibility and for a long period of time, and there has been available no product that can be satisfactorily used particularly in artificial blood vessels having an inner diameter of 6 mm of less.

Specifically, the tubes obtained by the melt extrusion process may form smooth inner and outer faces, whereby the the wall of a tube may be so dense that it can not be freely controlled. Also, as a matter of course, they may have practically a great disadvantage that a needle can run through them only with difficulty at the time of suturing. Application of such tubes in such use as in artificial blood vessels for which a long term compatibility with the blood and surrounding tissue is required, may not give any desired results even if there are used materials such as polyurethane and polyurethane urea having excellent antithrombotic properties. In other words, with a prolonged period of transplantation, such tubes may turn limy with lapse of time to form as a result a large quantity of thrombi around them. It is also known that application of such tubes having a smooth inner face as artificial blood vessels may result in no stable take on the inner face of an artificial blood vessel, of the intimal tissue extending from a cut end of the blood vessel on the side of the living body, to cause the peeling, and therefore the flow of blood may be disturbed at that portion to produce thrombi, which thrombi may again grow into tissue to bring about hypertrophy of an intima.

The dip process may result in not only a low dimensional precision with an uneven wall thickness, but also a multi-layered wall structure, which can not be freely controlled with good reproducibility. Specifically, since it is impossible to uniformly control the evaporation of a solvent in the polyurethane solution applied on the mold for every dipping, the products may lack structural uniformity and those having high reliability can not be obtained.

The process disclosed in Japanese Unexamined Patent Publication No. 188164/1985 is characterized in that the solidification of the solution of a high molecular compound is carried out substantially from both sides of the inner face and outer face,, but otherwise has no difference at all from the conventional process for producing a hollow fibrous membrane, and can only produce a tube having skin layers on both of the faces since the solidification may proceed from the inside and outside of the tube. This process also requires a long period of time until the solidification reaches the state in which no deformation of the tube may occur. Accordingly, if a tube of large inner diameter is attempted to be produced, which may have poor shape stability, this process may have a disadvantage that deformation or ununiform solidification may readily occur in the course of taking-off, actually that a molded tube, having diameter more than 1 to 2 mm, may become oval.

For an artificial blood vessel having inner diameter of 7 mm or less, what is important is the coaptability with a living blood vessel, and delicate control of the properties is indispensable for improving the patency results. Especially, suitable flexibility is required in order for the inside of a living blood vessel and that of an artificial blood vessel to be smoothly joined each other at the time of suturing. Further, readiness in running-through of a suturing needle can improve the suturing performance, giving a great influence to the patency results. In other words, a good anastomotic performance is very important for making the flow path at a junction to a living blood vessel to have a desired shape. Properties also fundamentally necessary for the artificial blood vessels, which are used semipermanently, are such that a wall membrane must be as a matter of course endurable to the pulsational load by blood pressure to be applied 100,000 or more times a day, and also that a suture at which the stress may centralize may not be gradually dialated or broken.

There have been conventionally used artificial blood vessels produced by drawing polytetrafluoroethylene molded into a tube to have finely fibrous structure, which have been improved in the antithrombotic properties as compared with an artificial blood vessel produced by providing folds on a tube comprising woven polyester fiber. However, these not only have problems that a needle can run through only with difficulty and bleeding from needle holes may occur, but also have room for improvement in the coaptability with a living blood vessel.

In artificial blood vessels having inner diameter of 7 mm or less, particularly 6 mm or less, nothing has been available that can be used with clinically satisfactory patency results. Only a product obtained by making porous the above polytetrafluoroethylene has been used for limited purposes, which, however, shows unsatisfactory results in respect of the patent degree for more than one year. Thus, development of an artificial blood vessel having better patency has been sought after. In order to improve the patency results, it is first necessary and indispensable to improve the antithrombotic properties of a material. Further, the artificial blood vessel must be endowed with the above mechanical properties required as an artificial blood vessel. Next, it must retain the tube wall structure having excellent patency over a long term. Many experimental data have showed that the artificial blood vessel having the fine structure can not maintain the patent state for a long period of time as mentioned above. In particular, the intima growing at the inner face can not be stably retained, and may be repeatedly grown and peeled because of the blood flow or bending. Particularly at the junction to a living blood vessel, panni may abnormally grow, which may cause disturbance of blood flow, so that there may occur the growth of thrombi, which may gradually grow into tissue, resulting in the construction at the anastomosed portions. In order to achieve the stable take of intima, it is preferred that the inner face is provided with no skin layer and has concaves of 1 to 100 microns, preferably 3 to 20 microns, in diameter, and at the same time the concaves are open to the vacuole in the inside of a tube wall. Accordingly, the artificial blood vessel having the structure that the inner face is provided with no skin layer can not be produced by the known process in which the solidification is carried out from both of the inner face and outer face with use of an annular orifice.

As a process to avoid this problem, a proposal has been disclosed, for example, in Japanese Unexamined Patent Publication No. 188165/1985. That is a process in which a tube is molded while mixing a pore-forming agent in a solution, followed by removing the agent according to any suitable means to prevent a dense skin layer being formed on the inner face. This process, however, may be accompanied with a substantial disadvantage that not only the steps may be made very complicated but also the porosity of a blood vessel may become higher. Namely, the tube wall as a whole may become porous to cause exudation of plasma and bring about a complication such as seroma to worsen the prognosis. Similar phenomenon may frequently occur in the above mentioned artificial blood vessel made of polytetrafluoroethylene, thereby causing an infectious disease to necessarily require re-transplantation of the vessel, as well known. Needless to say, if on the other hand a pore-forming agent that may not cause any leakage of blood cell components from the tube wall is used, no stable take of tissue can be expected in the inner face of the artificial blood vessel.

It is preferable for an artificial blood vessel to have holes opened to the inside of a tube wall so that the stable take of intima on the inner face may be promoted, and at the same time have such dense structure on its outer face that may not allow not only blood cells but also plasma to pass therethrough. In addition to such a structural factor, it is necessary for an artificial blood vessel to be formed by use of a material that may have mechanically sufficient strength, may have substantial antithrombotic properties that can suppress the initial thrombus to a smaller quantity, and may not cause any strong histionic reaction or deterioration due to biodegradation even after a long term transplantation in a living body.

In order to eliminate the above-mentioned disadvantages pertaining to the conventional medical tubes, the present inventors have made intensive studies. As a result, they have succeeded in producing a medical tube having excellent compatibility with blood, particularly an artificial blood vessel having excellent patency. Thus the present invention has been accomplished.

SUMMARY OF THE INVENTION

The medical tube according to this invention is characterized by comprising a mono-layer medical tube comprising a high molecular weight compound, wherein inner texture of a tube wall constituting said tube is porous and no skin layer is present on the inner face of said tube wall.

In an embodiment of the above medical tube of this invention, the inner texture of the tube wall is constructed in such a state that a great number of cell or void walls constituting cells or void continuously connected, and the inner face of said tube wall comprises said continuously connected cell or void walls.

The above vacuolar walls may preferably be porous, having a great number of sufficiently smaller pores as compared with the above vacuoles. Such structure can be achieved by carrying out solidification with use of a production process according to a wet process as described hereinafter. The cell or void walls constituting the cells or voids in the medical tube of this invention have microscopicaly spongy structure in which minute pores of 0.01 to 30$\mu$ are present, whereby tissue may readily grow to give higher remedial effect.

Since the medical tube of this invention has special inner texture and has no heterogeneous skin structure, there can be achieved excellent compliance (or mechanical adaptability), excellent compatibility with a living body, and stabilization of viable endothelia. Thus, this invention can provide for the first time a medical tube that can retain the mechanical properties, for example, strength and fatigue resistance inherent in the material used, may not cause any plastic deformation with time lapse after transplantation, may have no rigidness the conventional medical tubes have had wherein dense portions have been present in the inner texture, and may have excellent mechanical properties, compliance and tissue-formation stability altogether.

DESCRIPTION OF THE PREFERRED EMBODIMENTS

In the medical tube of this invention, wherein the inner texture of the tube wall is constructed in such a state that a great number of cell or void walls constituting cells or voids continuously connected over the whole area of the texture, the size of said cells or voids may be in the corresponding to the maximum diameter taken at an arbitrary cross-section, relative to the thickness of the wall (d) is preferably;

$$0.005d \leq 1 \leq 0.9\ d$$

more preferably;

$$0.01d \leq 1 \leq 0.8\ d.$$

The value of l more than 0.9 d may result in overly low mechanical strength from a viewpoint of practical use to give anxiety for clinical use, and the value of l less than 0.005 d may result in achieving no desired compliance.

Another feature of the medical tube of this invention is that it has very good suturing performance. The grade of the suturing performance may often affect the patency of a transplanted blood vessel. If a blood vessel is sutured in a bad state, a blood flow may be disturbed at the sutured portion to make a trigger of the formation of thrombi, whereby the obturation of the transplanted blood vessel may be brought about. A tube comprising a high molecular compound and being made porous the inner texture of its tube wall as in the present invention may achieve both an adequate elongation and flexibility of the texture, whereby a sutural needle can readily run through and the suturing can be performed with ease to smoothly anastomose the tube to a host blood vessel.

It is a matter of interest that the artificial blood vessel whose inner texture of the tube wall is porous may not be torn at the sutured portion, and there has been perfectly eliminated the disadvantage that a tear may develop from a suture as in the conventional polyurethane artificial blood vessel having a dense portion in the above inner texture. It is also an interesting phenomenon that no blood may leak from the suture. This is presumably owing to the elasticity inherent in polyurethane or the like and, in addition thereto, the pore effect attained by a multiple overlap of a great (number of cell or void walls constituting cells or voids.

Anastomosing the medical tube of this invention to a host blood vessel, the inner texture may become a cell or void texture having been made mutually continuous between the both ends of the tube, whereby tissue may be readily invaded from the anastomosed portion to achieve very excellent anastomosed portion curability, and also, the inner face of the tube wall constituting the artificial blood vessel may have no skin layer, whereby it can be suited for the growth of intimal tissue and can readily turn into an organic body. This is considered to be a factor of the very good long term patency possessed by the medical tube of the present invention.

The distribution of the cells or voids when viewed at a cross-section of the tube wall constituting the medical tube of this invention may be made in such a manner that the size of the cells or voids becomes smaller at the part near to its outside, whereby it is made possible to minimize the leakage of blood from the sutured portion to obtain very good results of an operation. This can be achieved by effecting the solidification from the outside only, at the time of the production of the medical tube of this invention.

The high molecular weight compound used in this invention comprises a substance having excellent compatibility with blood or tissue, namely, a polymer that may not have any acute and chronic toxicity, heat build-up and hemolyticity, and may not cause any inflammation in the surrounding tissue even under a long term transplantation. Such a polymer may include, for example, polyvinyl halides, polystyrene and derivatives thereof, polyolefin polymers, polyester condensates, cellulose macromolecules, polyurethane macromolecules, polysulfone, resins, polyamide macromolecules, etc. It of course may include copolymers or mixtures mutually containing these. Among these, polyurethane type polymers are preferred in view of the mechanical properties, the stability in a living body and the anti-thrombotic properties. Examples thereof may include polyurethane, polyurethane urea, a blend of these with silicone polymer or a product wherein these are mutually invaded to form a network structure. These may also include segmented polyurethane or polyurethane, urea, a produce containing polydimethyl siloxane in the backbone chain, and a product containing fluorine in a hard or soft segment. From a viewpoint of the hardness to biodegradation, polyether type polyurethane or polyurethane urea is more preferable than polyester type one.

Most preferable as the polyether constituting the polyether segment of the above polyurethane or the like is polytetramethylene oxide., buy other polyalkylene oxides may be also preferable (provided that they have 2.and/or 3 carbon atoms in the alkylene moiety). Examples of such polyalkylene oxides may include polyethylene oxide, polypropylene oxide, an ethylene oxide/propylene oxide copolymer or block copolymer. There may be also used polyurethanes containing in the same backbone chain a polytetramethylene oxide segment and polyalkylene oxide (having 2 and/or 3 carbon atoms in the alkylene moiety) to have both the hydrophilic nature and mechanical properties. This polyurethane have preeminently good antithrombotic properties and living body compatibility, and is a new type polyurethane the present inventors have found, having good compatibility with a living body.

The polyether constituting these soft segments may have a molecular weight usually ranging between 400 and 3,000, preferably 450 and 2,500, and more preferably ranging between 500 and 2,500. Of these, a best polyether segment is a polytetramethylene oxide chain having a molecular weight of 800 to 2,500, particularly a molecular weight of 1,300 to 2,000. The molecular weight more than 3,000, of the polyether soft segment may result in poorness of the mechanical strength of the polyurethane artificial blood vessel, and the same less than 400 may make a molded artificial blood vessel too rigid to be used.

The synthesis of polyurethane may be carried out by use of a conventional method comprising allowing the above polyether terminated with hydroxyl groups at its both ends to react with a known diisocyanate used for the synthesis of polyurethane, including 4,4'-diphenylmethane diisocyanate, toluidine diisocyanate, 4,4'-dicyclohexylmethane diisocyanate, hexamethylene diisocyanate, etc. to produce an isocyanate-terminated prepolymer, and subjecting it to chain extension with use of a diamine such as ethylene diamine, propylene diamine and tetramethylene diamine or a diol such as ethylene glycol, propylene glycol and butanediol.

In the medical tube according to this invention, the inner texture of the tube wall constituting said tube is porous and no skin layer is present on the inner face of said tube wall. Accordingly, in addition to the living body compatibility inherent therein, the texture is endowed with the softness, whereby the suturing can be readily performed and, as a result, no pannus may be generated at the anastomosed portion. Also, excellent compliance can be imparted to the present medical tube. Accordingly, when it is used as an artificial blood vessel, it can undergo appropriate elastic deformation along with the beat of the heart to moderate the stimulation by blood against a host blood vessel. Further, there is no skin layer in the inner face of this blood vessel and tissue may readily invade the vacuoles, whereby excellent curability can be achieved. Thus, a road has been opened to an artificial blood vessel having an inner diameter of 6 mm or less and retaining excellent patency.

The medical tube of the present invention can be prepared, for example, in the following manner.

Namely, it can be produced by a process comprising thrusting forward a core rod having a round cross-section and made of a rigid body from a circular orifice to extrude a solution of a high molecular compound from a gap slit defined between said orifice and said core rod in such a manner that the solution is spread over the whole surface of said core rod, and leading the core rod in a solidifying medium to solidify said high molecular compound around said core rod, followed by taking out said core rod.

The solution used for the molding may be preferably made to have the viscosity of 5 poises or more at a molding temperature. The viscosity less than 5 poises may cause the formation of a giant vacuole in the inside of the tube wall to lower the strength. Uneven wall thickness may also be brought about in the course of the molding. There may be advantageously less limitation to the molding condition at the viscosity of 10 poises or more.

On the other hand, there is almost no limitation in the higher side of the viscosity, and the molding can be sufficiently achieved even with low fluidity of the solution. It is one of the features of the process according to this invention that the molding can be readily carried out even with use of the solution of about 5,000 poises at which the molding could be carried out only with great difficulty according to a hollow fiber production process employing a conventional annular nozzle. However, since it is desired from the viewpoint of production to relatively simply achieve the deaeration of the solution, the solution may preferably have the viscosity of 3,000 poises or less, more preferably 2,000 poises or less.

In the production process of this invention, as a solvent used for the solution of high molecular weight compound, know solvent can be easily selected corresponding to the respective substances to be used. However, a water-soluble solvent is advantageous in order to prevent the solvent remaining in a product and from a viewpoint of the cost in the production steps. Such a solvent may include, for example, dimethylformamide, dimethylacetamide, demethylsulfoxide, N-methyl-2-pyrrolidone, dioxane, tetrahydrofran, acetone, etc. In the production process of this invention, the solution may not necessarily be in a good solubilized state. For this reason, a poor solvent or a swelling agent such as urea may be mixed and used in a large amount. This is very advantageous in the production of the medical tube, particularly the artificial blood vessel, aimed at in this invention. Namely, the solvent system can be selected in a wide range, whereby the porosity (the degree of being porous) can be widely varied with ease and without any particular complicated steps such as a step of using a pore-forming agent.

In the production process of this invention, the rod comprising a rigid body used as the core may be made of a substance that may not dissolve in the solution and may not readily change in its shape while it is led in the solidifying medium. As the corrosion resistance is also required, particularly preferred are materials applied with chrome plating or Teflon processing on stainless steel, steel, brass, etc.

The core rod thrust forward in such a state that the solution is spread over the whole peripheral surface is directly, or after passing through a cetain dry section, led in the solidifying medium.

Specifically, there can be used any of the wet solidification according to which the high molecular weight compound solution discharged from the gap slit defined between the round orifice and the core rod is directly fed in a water system solidifying medium, and the dry and wet solidification according to which the same is led in the water system solidifying medium via a dry section.

In the case a known method for spinning a hollow fibrous film is applied in the production of something having a large diameter and wall thickness like the artificial blood vessel, it is difficult to maintain the shape to a desired state unless rapid solidifying action is applied from both the inner face and outer face. Accordingly, the condition such that the strong solidifying action may be applied from both the inner face and outer face is indispensable for stably producing a tube. However, this becomes a great obstacle to the desired structure to be made up as an artificial blood vessel. Namely, it follows that the structure which is more denser than the inside of the tube wall is formed on surfaces of the inner face and outer face.

These disadvantages have been removed by the production process of this invention. That is to say, since the rigid body present in the inside can play a role of stably retaining the surrounding solution, it has been made possible to produce with good reproducibility a tube having a uniform shape and size by only the solidification from the outer face.

There is no problem in the molding even if the rate of the solidification from the outer face is lowered, and the solidification can be achieved over a sufficiently long time.

Since it is possible in the process of this invention to widely vary the solidification conditions, the degree of freedom of molding can be made great, and molded products of various types of structure can be produced.

To the solidifying medium, a solvent, a poor solvent and a salt, for example, may be added, whereby the structure of both the inner face and outer face, or of the outer face, can be widely varied.

Also, the surface energy of the rigid body used as the core may be varied by selecting the quality of materials or by applying means such as coating of Teflon, silicone, etc., whereby not only the microscopic properties that may affect the antithrombotic properties but also the morphological surface state can be varied.

One of the remarkable features of the production process of this invention is that, when the dry and wet solidification is carried out, the time for passing through the dry section can be very strictly controlled. In particular, it is possible to precisely control the dry section passing time even to such a time as short as 0.01 to several ten seconds. This is very important to make uniform the structure of the outer wall of a molded tube, and is greatly different from the conventionally known dip process.

From the foregoing reason, it is preferred to provide the dry section, whereby it is possible to readily obtain a smooth outer face by utilizing the surface flow of the solution of high molecular compound in the dry section. Optimum length of the dry section may be determined chiefly depending on the viscosity of the solution and the volatility of the solvent, and may be preferably in the range of 5 to 300 mm in usual cases. The length less than 5 mm may result in insufficiency of the above-mentioned surface-smoothing effect. The length more than 300 mm may cause dripping of the solution to give a product having an ununiform section or a thickness gradually varied in the longitudinal, direction. In the case the high molecular weight compound solution contains a solvent having high volatility, the evaporation of the solvent from its surface may occur rapidly, and, as a result, the surface may reach a dew point to cause a phenomenon such as the condensation of minute waterdrops, and severe control of the environmental conditions may be required.

From the foregoing reason, the length of the dry section may be preferably in the range of 20 to 200 mm.

The rate of extrusion at the time the core rod passes through the dry section may be usually in the range of 1 to 300 mm/sec, preferably 5 to 200 mm/sec, and more preferably 10 to 100 mm/sec. The extrusion rate exceeding 300 mm/sec may tend to cause a distortion due to the residual stress in a post-treatment step, and the rate less than 1 mm/sec may cause non-uniform structure in the outer surface depending on the atmospheric temperature and humidity or the concentration of the solvent.

As the solidifying medium, there may be preferably used the one having excellent compatibility for the purpose of the removal of the solvent. From viewpoints of the safety and cost, particularly preferred is water. There may be optionally used lower alcohols such as methanol-, ethanol- and isopropanol-denatured alcohols. In any case, for the purpose of perfect removal of the solvent, a solvent that can be finally replaced by water may be preferably used in the solidifying system. For example, in the case water is used as the solidifying medium, there can be obtained a product having the structure usually rougher at the portion near to the inner face than the portion near to the outer face, and the inner face, on which no solidification is applied at all can have the above rough face structure comprising concaves of about 1 to 100 microns in diameter necessary for the inner film to be kept thin and stable without formation of any heterogeneousdense layer. The concaves are open to the cell or void in the inside and may contribute the stabilization of the intima.

The resulting solidified molded product, after the solvent is thoroughly removed therefrom, may be sterilized after air-drying or forced drying, or may be substituted with a physiological saline solution as it is in a wet state, and then sterilized in an autoclave or by gamma rays.

When polyurethane or polyurethane urea is used, the porous structure can give a desired compliance (C), which can be defined by the following formula:

$$C = (\Delta V)/(V_o \cdot \Delta P) \times 100 (\%)$$

wherein
$V_o$ is the internal volume of a measured blood vessel under internal pressure of 50 mmHg;
$\Delta P$ is a changed portion 100 mmHg when the internal pressure changed from 50 mmHg to 150 mmHg; and $\Delta V$ is the internal volume of the measured blood vessel, increased when the internal pressure changed from 50 mmHg to 150 mmHg.

If the compliance represented by the value defined as above is more than 65%, the irreversible expansion of inner cavities may be gradually caused due to repeatedly applied stress of blood pressure during long-term enthesis. Also, if this value is overly low, particularly 1% or less, abnormal expansion may be brought about on the side of a host blood vessel, and, as a result, the blood flow may be disturbed in the vicinity of an anastomosed portion to give a main cause of the hypertrophy of intima at the anastomosed portion.

Accordingly, the thickness of extrusion and the polymer concentration in the solution may be preferably fixed in advance in the manner that the above compliance may be usually 1 to 65%, preferably 3 to 20%, and more preferably 3 to 10%.

The core rod may be also in advance covered with a reinforcing material such as a mesh made of polyester before the process of this invention is carried out so that the above reinforcing material may be embedded in the inside, or, alternatively, the core rod may be thinly coated with other material before the process of this invention is carried out.

Figure 1:
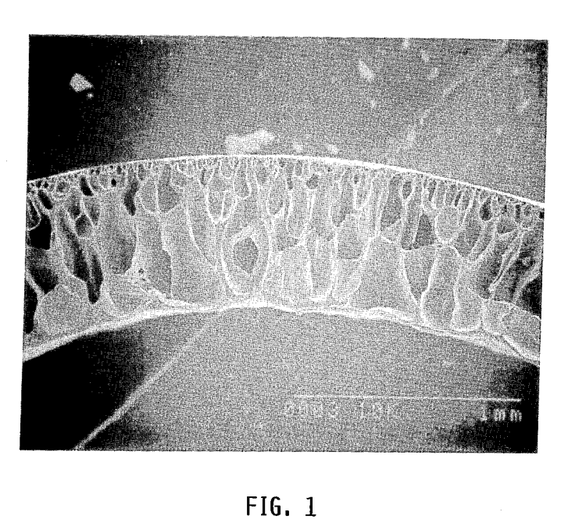
FIGS. 1 and 2 are cross-sectional views of a medical tube according to an embodiment of the invention.
Figure 2:
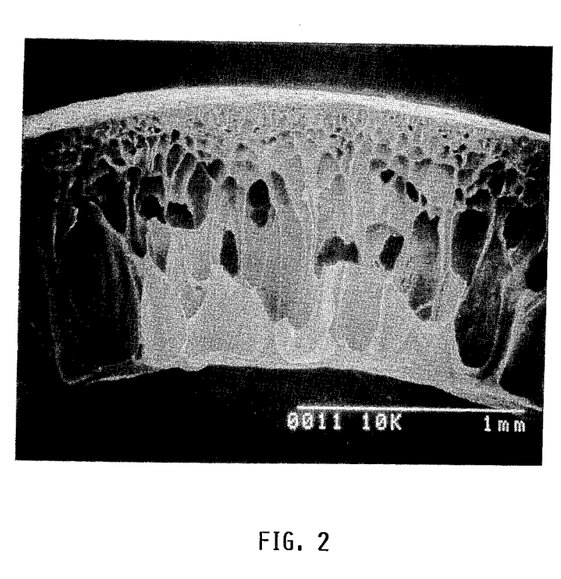
Figure 3:
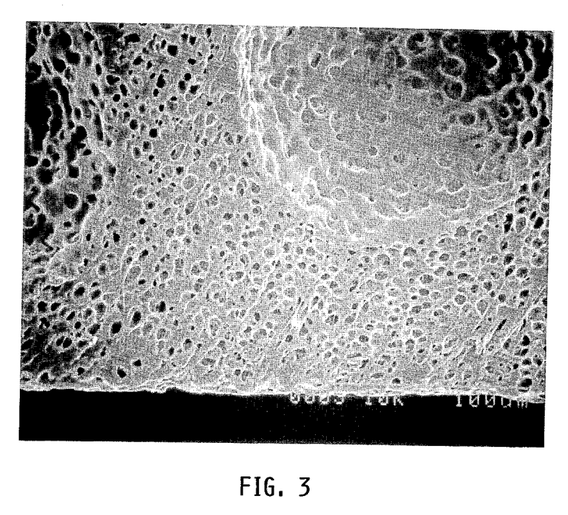
FIG. 3 is cross-sectional view similar to FIGS. 1 and 2 but enlarged more than ten times.
Figure 4:
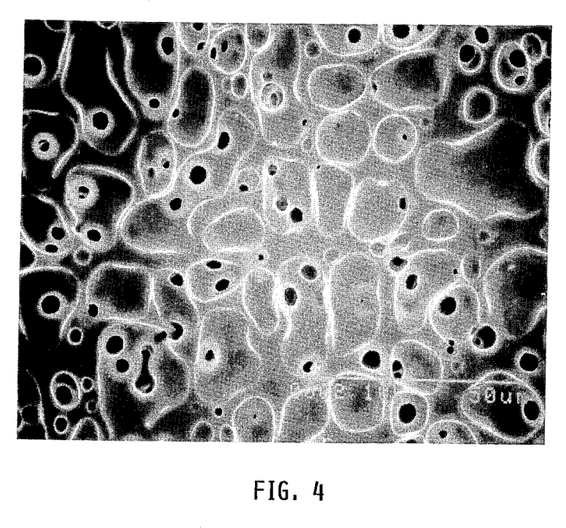
FIG 4 is a plan view of the inner face of a medical tue according to the present invention.

This invention will be described below in greater detail by Examples, but the scope of this invention is by no means limited by these Examples.

The "%" shown in the following refers all to "% by weight" unless particularly mentioned.

EXAMPLE 1

Polytetramethylene glycol terminated with hydroxyl groups at its both ends and having a molecular weight of 1650 was reacted with 4,4'-diphenylmethane diisocyanate to give a both end isocyanate-terminated prepolymer, which was subjected to chain extension with use of butanediol to synthesize polyurethane. The polyurethane thus synthesized was purified by repeating re-precipitation three times in a tetrahydrofuran/ethanol system. The purified polyurethane was dissolved in dimethylacetamide to give a 18.3% solution.

From a round orifice of 10 mm in diameter, a stainless steel rod of 8 mm in diameter having been precisely set to be concentric with this orifice was thrust forward at a constant speed, and the above polyurethane solution was uniformly extruded from the uniform gap between the stainless steel rod thus thrust forward and the orifice so that the solution may be spread over the whole peripheral surface of the rod, which rod was then led in water kept at 30° C. to effect solidification. Here, since the core comprises a stainless steel rod, the solidification is effected from the outside only. After 3 hours, this rod was taken out and further dipped overnight in flowing water to remove solvent. A polyurethane tube thus solidfied was peeled from the stainless steel rod, and then air-dried.

The resulting polyurethane tube had porous structure of milk-white color, and the cross-section of its tube wall was in such a state that a great umber of cell or void constituting cells or voids is continuously connected. The tube wall was 0.7 mm thick and had inner diameter of 7 mm with a slight shrinkage produced at the time of the air-drying. No heterogeneous skin layer was present on the inner face of the tube wall of the polyurethane artificial blood vessel thus obtained, and also any of the vacuoles were not open and directly exposed to the inner face of the tube wall. Accordingly, the inner face of the tube wall had microscopically spongy structure in which minute pores were present as in the case of the cell or void walls in the inner texture of this artificial blood vessel. A scanning electron microscopic observation enlarged to 200 magnification confirmed that the inner face of the tube wall had substantially the same physical structure with the cell or void wall in the inner texture of this artificial blood vessel, and there was seen no difference between the both. The inner face of the tube wall of this artificial blood vessel had the structure that may not cause any swirling of the blood flow which is considered to be caused when the vacuoles are open and directly exposed to the inner face of the tube wall. Also, the cells or voids were relatively larger in the inside of the tube, which were relatively smaller in the vicinity of the outer face of the tube wall. The compliance value was 45%. The polyurethane tube obtained in this Example was filled with water, which water was kept under positive pressure of 120 mmHg. A cannula (needle diameter: 1.5 mm) used for extracorporeal blood circulation in an artificial dialysis was repeatedly sticked 150 times at random position extending over 15 cm of the above tube to examine the state of water leakage. There was seen no water leakage even after the sticking as many as 150 times.

EXAMPLE 2

Entirely the same experiment as in Example 1 was carried out, except that a stainless steel of 4 mm in outer diameter was used in this Example. As a result, there was obtained a tube having tube wall inner diameter of 3.2 mm, tube wall thickness of 0.5 mm and the compliance of C=64% to have the tube wall inner texture structured in such a state that a great number of cell or void wall constituting cells or voids is continuously connected.

The inner face of the tube wall of the tube according to this Example was comprised of the above cell or void walls continuously connected, as in the case of the tube according to Example 1, and no skin layer (a denser layer) was present on the inner face.

This tube was used as an artificial blood vessel, which was transplanted by end-by-end suturing to the iliac artery and the femoral artery of a hybrid adult dog. Anastomosis was very readily carried out with appropriate flexibility and compliance (39%), and there was seen no bleeding from the sutured portions. Animal experiments were carried out for six cases under the same conditions, but any of the transplanted blood vessels were still patent even after 16 months.

EXAMPLE 3

Polytetramethylene glycol terminated with hydroxyl groups at its both ends and having a molecular weight of 1650 was reacted with 4,4'-diphenylmethane diisocyanate to give a both end isocyanate-terminated prepolymer, which was subjected to chain extension with use of butanediol to synthesize polyurethane. The polyurethane thus synthesized was purified by repeating reprecipitation three times in a tetrahydrofuran/ethanol system. The purified polyurethane was dissolved in dimethylacetamide to give a 20.0% solution.

From a round orifice of 10 mm in diameter, a stainless steel rod of 7 mm in diameter having been precisely set to be concentric with this orifice was thrust forward at a constant speed, and the above polyurethane solution was uniformly extruded from the uniform gap between the stainless steel rod thus thrust forward and the orifice so that the solution may be spread over the whole peripheral surface of the rod, which rod was then led in water kept at 20° C. to effect solidification. Here, since the core comprises a stainless steel rod, the solidification is effected from the outside only. After 10 hours, this rod was taken out and further dipped overnight in flowing water to remove solvent. A polyurethane tube thus solidified was peeled from the stainless steel rod, and then air-dried.

The resulting polyurethane tube had porous structure of milk-white color, and the cross-section of its tube wall was in such a state that a great number of vacuolar walls constituting vacuoles is continuously connected. The tube wall was 1.1 mm thick and had inner diameter of 6.5 mm with a slight shrinkage produced at the time of the air-drying. No heterogeneous skin layer was present on the inner face of the tube wall of the polyurethane artificial blood vessel thus obtained, and also any of the cells or voids were not open and directly exposed to the inner face of the tube wall. Accordingly, the inner face of the tube wall had microscopically spongy structure in which minute pores were present as in the case of the cell or void walls in the inner texture of this artificial blood vessel. A scanning electron microscopic observation enlarged to 200 magnification confirmed that the inner face of the tube wall had substantially the same physical structure with the cell or void walls in the inner texture of this artificial blood vessel, and there was seen no difference between the both. The inner face of the tube wall of this artificial blood vessel had the structure that may not cause any swirling of the blood flow which is considered to be caused when the vacuoles are open and directly exposed to the inner face of the tube wall. Also, the cells or voids were relatively larger in the inside of the tube, which were relatively smaller in the vicinity of the outer face of the tube wall. The compliance value was 25%. The polyurethane tube obtained in this Example was filled with water, which water was kept under positive pressure of 275 mmHg, but there was seen no water leakage from the tube wall.

EXAMPLE 4

Entirely the same experiment as in Example 3 was carried out, except that a stainless steel of 4.5 mm in outer diameter was used in this Example. As a result, there was obtained a tube having tube wall inner diameter of 4.0 mm, tube wall thickness of 0.5 mm and the compliance of C=19% to have the tube wall inner texture structured in such a state that a great number of cell or void walls constituting cells or voids is continuously connected.

The inner face of the tube wall of the tube according to this Example was comprised of the above cell or void walls continuously connected, as in the case of the tube according to Example 3, and no skin layer (a denser layer) was present on the inner face.

This tube was used as an artificial blood vessel, which was transplanted by end-by-end suturing to the iliac artery and the femoral artery of a hybrid adult dog.

As compared with a commercially available artificial blood vessel made of Teflon, there was achieved better running-through of needles and adhesion to host blood vessels, and also seen no bleeding after operation at all from the needle holes and anastomosed portions under systemic heparinization of 1,000 units. In experiments using three cases, there was shown good patency in all cases after lapse of 18 months.

COMPARATIVE EXAMPLE 1

Using the polyurethane solution used in Example 1, the solution was extruded from an annular nozzle (dimensions of the solution outlet: 3 mm in inner diameter, 5 mm in outer diameter) at the rate of about 40 cm/min with use of a gear pump, and, at the same time, water having been deaerated beforehand was discharged from the inside center of the solution extruded in the annular form. The discharge amount of the water was 1.2 times the extrusion amount of the polyurethane solution. A linear body extruded with inclusion of this water in its inside was immediately led in water to solidify the polyurethane in the shape of a tube, which was further allowed to stand as it was for 1 hour.

The tube thus obtained had inner diameter of about 3 mm, outer diameter of about 4.2 mm, and, since this was solidified from both sides of the inside and outside, had skin layers on both the inner face and outer face of the tube wall, which are of different nature from, and denser than, the inner texture of the tube wall. This is a distinguishable feature different from the tubes obtained in Examples 1 and 2 mentioned above. The tubes obtained in Examples 1 and 2 had no skin layer in the inner face of the tube wall, and had a thin skin layer only on the outer face. Whereas, the tube according to this Comparative example 2 in the respect of the appearance of a cross-section of the tube wall. Using the tube similar to that in Example 2 in respect of the appearance of a cross-section of the tube wall. Using the tube according to this Comparative Example, transplantation was carried out to hybrid adult dogs under the same conditions as in Example 2. Among 4 cases of transplanted blood vessels, obturation occurred in 3 cases after a month and in one case after 3 months.

The dogs were caused to sacrificially die, and autopsies made on kidneys revealed that obturation occurred in the capillaries of kidneys. Similar autopsies were made on the dogs in Example 2, but no abnormality was seen in kidneys.

COMPARATIVE EXAMPLE 2

Using the polyurethane solution used in Example 3, the solution was extruded from an annular nozzle (dimensions of the solution outlet: 3 mm in inner diameter, 5 mm in outer diameter) with use of a gear pump, and, at the same time, water having been deaerated beforehand was discharged from the inside center of the solution extruded in the annular form. The discharge amount of the water was 1.2 times the extrusion amount of the polyurethane solution. A linear body extruded with inclusion of this water in its inside was immediately led in water to solidify the polyurethane in the shape of a tube, which was further allowed to stand as it was for 1 hour.

The tube thus obtained had inner diameter of about 3.3 mm, outer diameter of about 4.8 mm, and, since this was solidified from both sides of the inside and outside, had skin layers on both the inner face and outer face of the tube wall, which are of different nature from, and denser than, the inner texture of the tube wall. This is a distinguishable feature different from the tubes obtained in Examples 3 and 4 mentioned above. The tubes obtained in Examples 3 and 4 had no skin layer in the inner face of the tube wall, and had a thin skin layer only on the outer face. Whereas, the tube according to this Comparative Example showed the spongy-like structure similar to that in Example 4 in respect of the appearance of a cross-section of the tube wall. Examination on the longitudinal cross-section of the tube revealed that it had turned flat and the rectangular two inner diameters X and Y were in the relation of $X/Y=1.30$. Using the tube according to this Comparative Example, transplantation was carried out to hybrid adult dogs under the same conditions as in Example 4. Among 2 cases of transplanted blood vessels, obturation occurred in one case after 3 months. In another case, the dog was sacrificially dead, and, as a result of an observation, there was seen a pannus of about 1 mm at the anastomosed portion and new thrombi was formed around it in a large quantity.

EXAMPLE 5

From polytetramethylene glycol terminated with hydroxyl groups at its both ends and having a molecular weight of 1,890, and 4,4'-dicyclohexylmethane diisocyanate, a both end isocyanate group-terminated prepolymer was produced according to a conventional method, which prepolymer was subjected to chain extension with use of ethylenediamine to synthesize polyurethane urea. This was purified by repeating reprecipitation three times in a dimethylformamide/ethanol system.

This polyurethane urea was dissolved in dimethylformamide to give a solution of 20% concentration. A stainless steel rod of 5 mm in outer diameter was concentrically thrust forward from an orifice of 7.2 mm in diameter, and the above solution was uniformly extruded from the uniform gap defined between the stainless steel rod thus thrust forward and the orifice so that the solution may be spread over the whole peripheral surface of the rod, which rod was then led in water kept at 10° C. while synchronizing the flow rate of the polyurethane solution and the extrusion rate of the stainless steel rod. The polyurethane urea tube thus extruded was solidified slowly from the outside, namely, the outer face, whereby a white polyurethane film was formed after about 30 minutes around the stainless steel rod. This was allowed to stand for 24 hours to complete the solidification, and further dipped in flowing water for 20 hours to perfectly remove dimethylformamide. The resulting polyurethane urea tube was peeled from the stainless steel rod and air-dried at room temperature.

This polyurethane urea tube had, after drying, inner diameter of 3.6 mm and tube wall thickness of 0.6 mm, and the cross-section of the tube wall had substantially the structure such that a great number of cell or void walls constituting cells or voids was continuously connected over its whole body except for a thin skin layer on the outer face of the tube wall. More specifically, similar to the tube according to Example 1, the cross-sectional structure of the tube wall was in such a state that a great number of cell or void walls constituting cells or void was continuously connected except for the above skin layer, and the inner face thereof comprised said continuously connected cell or void walls. The compliance value of the artificial blood vessel according to this Example was 62%.

This tube had appropriate softness, elasticity and compliance, and was easy to handle. Using this tube as an artificial blood vessel, an artery-vein bypass operation to transplant it as a bypass between the femoral artery and the femoral vein of a hybrid adult dog was carried out. The connection was in accordance with the end-by-side connection, and the bypass had the whole length of 20 cm. There was shown a very good suturing performance, with ready running-through of a needle and without any blood leakage after suturing. The present bypass tube was still patent even after lapse of 6 months.

EXAMPLE 6

From polytetramethylene glycol terminated with hydroxyl groups at its both ends and having a molecular weight of 1,890, and 4,4'-dicyclohexylmethane diisocyanate, a both end isocyanate group-terminated prepolymer was produced according to a conventional method, which prepolymer was subjected to chain extension with use of ethylenediamine to synthesize polyurethane urea. This was purified by repeating reprecipitation three times in a dimethylformamide/ethanol system.

This polyurethane urea was dissolved in dimethylformamide to give a solution of 33% concentration (viscosity at 20° C.: 4,300 poises). A stainless steel rod of 5 mm in outer diameter was concentrically thrust forward from an orifice of 8.0 mm in diameter, and the above solution was uniformly extruded from the uniform gap defined between the stainless steel rod thus thrust forward and the orifice so that the solution may be spread over the whole peripheral surface of the rod, which rod was then led in water kept at 20° C. while synchronizing the flow rate of the polyurethane solution and the extrusion rate of the stainless steel rod. The polyurethane urea tube thus extruded was solidified slowly from the outside, namely, the outer face, whereby a white polyurethane film was formed after about 30 minutes around the stainless steel rod. This was allowed to stand for 24 hours to complete the solidification, and further dipped in flowing water for 20 hours to perfectly remove dimethylformamide. The resulting polyurethane urea tube was peeled from the stainless steel rod and air-dried at room temperature.

This polyurethane urea tube had, after drying, inner diameter of 4.4 mm and tube wall thickness of 0.6 mm, and the cross-section of the tube wall had substantially the structure such that a great number of cell or void walls constituting cells or voids was continuously connected over its whole body except for a thin skin layer on the outer face of the tube wall. More specifically, similar to the tube according to Example 3, the cross-sectional structure of the tube wall was in such a state that a great number of cell or void walls constituting cells or voids was continuously connected except for the above skin layer, and the inner face thereof comprised said continuously connected vacuolar walls. The compliance value of the artificial blood vessel according to this Example was 25%.

This tube had appropriate softness, elasticity and compliance, and was easy to handle. Using this tube as an artificial blood vessel, an artery-vein bypass operation to transplant it as a bypass between the femoral artery and the femoral vein of a hybrid adult dog was carried out. The connection was in accordance with the end-by-side connection, and the bypass had the whole length of 20 cm. There was shown a very good suturing performance, with ready running-through of a needle and without any blood leakage after suturing. The present bypass tube was still patent even after lapse of 6 months.

COMPARATIVE EXAMPLE 3

In the solutions of polyurethane and polyurethane urea used in Example 1 and Example 5, stainless steel rods of 4 mm and 5 mm in outer diameter, respectively, were subjected to a conventionally known process, namely, a dip and dry process repeated 10 times or more, to obtain corresponding polyurethane and polyurethane urea tubes.

These tubes had transparency, and, different from the tubes according to the above respective Examples, the inner texture of their tube walls was not, in such a state that a great number of cell or void walls constituting cells or voids was continuously connected, and most part of the texture was rather dense. The tubes were hard, had poor flexibility, and lacked compliance.

For reference, these tubes in this Comparative Example 3 were transplanted to hybrid adult dogs in the same manner as in Examples 2 and 5, but were hard to suture because of the hardness and the poor flexibility. Blood leakage also occurred from needle holes after suturing, resulting in the obturation of the transplanted tubes in a week.

COMPARATIVE EXAMPLE 4

In the solutions of polyurethane and polyurethane urea used in Example 3 and Example 6, stainless steel rods of 4 mm and 5 mm in outer diameter, respectively, were subjected to a conventionally known process, namely, a dip and dry process repeated 10 times or more, to obtain corresponding polyurethane and polyurethane urea tubes.

These tubes had transparency, and, different from the tubes according to the above respective Examples, the inner texture of their tube walls was not comprised in such a state that a great number of cell or void walls constituting cells or voids was continuously connected, most part of the texture being rather dense. The tubes were hard, had poor flexibility, and lacked compliance.

For reference, these tubes in this Comparative Example 4 were transplanted to hybrid adult dogs in the same manner as in Examples 4 and 6, but was hard to suture because of the hardness and the poor flexibility. Blood leakage also occurred from needle holes after suturing, resulting in the obturation of the transplanted tubes in a week.

COMPARATIVE EXAMPLE 5

The solution used in Example 6 was extruded from an annular nozzle of the same type as used in Comparative Example 2, and water was poured in its inside similarly.

Because of high viscosity of the solution, the back pressure raised up to 8 kg/cm$^2$. Discharge spots were seen on the outer surface of the resulting tube, and also the inner diameter cyclically changed in the range of 3.0 to 3.5 mm.

EXAMPLE 7

The solution same as in Example 3 was extruded by use of the same nozzle and stainless steel rod, passed through a dry section of 200 mm long, and thereafter led in the solidifying medium.

The tube obtained in the present Example had an outer face having superior smoothness as compared with the one obtained in Example 3, such that when measuring the outer diameter of the tube of 10 cm long, sectionally cut by every 5 mm, the 95% confidence interval was 7.55 to 7.67 in the present, Example, while it was 7.43 to 7.75 with greater deviation in the case where no dry section was provided.

EXAMPLE 8

The solution same as in Example 3 was extruded by use of the same nozzle and stainless steel rod, passed through a dry section of 100 mm long at the rate of 50 mm per second, and thereafter led in the solidifying medium.

After solidifying overnight in a flowing water medium, the core rod was drawn out, and the product was boiled in boiled water for 30 minutes, followed by drying at 45° C. The resulting artificial blood vessel was in the shape of a straight tube without any bend or knee and also without any deformation such as wrinkling on the surface.

COMPARATIVE EXAMPLE 6

Example 8 was repeated except that the dry section passing rate was made to be 320 mm per second, to obtain a dried artificial blood vessel. This shrinked in the longitudinal direction, and a great number of fine wrinkles was seen on its outer surface.

EXAMPLE 9

The polyurethane used in Example 3 was dissolved in dimethylacetamide to make a 10% solution. This solution was molded with use of a stainless steel rod covered beforehand with a polyester mesh of 5 mm in outer diameter, and a nozzle of 7 mm in diameter.

The polyester mesh was perfectly wet with the polyurethane solution, embedded in the sectional inside, and was not exposed to any of the inner face and outer face.

This tube had the compliance value of 4%, and there was seen no irreversible morphological change even under internal application of pressure of 500 mmHg for a month.

EXAMPLE 10

A core rod thrust forward under the same conditions as in Example 7 was led in a physiological saline solution, dipped therein overnight, washed with flowing water, and dried. The resulting tube had an outer surface with remarkably less irregularities as compared with the one obtained in Example 7, and there was observed almost no ruggedness even in an image enlarged to 5,000 magnification.

Thus, this invention can provide a medical tube having excellent long term patency.

We claim:

1. A medical tube comprising a mono-layer medical tube having inner and outer wall faces and comprised of a high molecular weight compound, wherein an inner texture of a tube wall constituting said tube is porous and no skin layer is present on the inner face of said tube wall;

the porous inner texture of the tube wall having a microscopically spongy structure wherein the pores are 0.01 to 30 microns, said inner structure defining a great number of cell or void walls forming cells or voids; said cells or voids continuously connected over the whole area of the inner texture by said pores, the size of said cells or voids being such that a diameter (1) of a cell or void corresponding to the maximum diameter taken at an arbitrary cross-section, relative to a thickness of the tube wall (d) is $0.005d \leq 1 \leq 0.9d$, and the size distribution within the tube being such that the size of the cells or voids are smaller near the outer wall of the tube thereby to minimize blood leakage;

said inner face further defining concavities open to the inside of the tube and open to said cells or voids; and wherein said medical tube shows no leakage of water when kept under a positive pressure of 120 mmHg.

2. The medical tube according to claim 1, wherein said high molecular weight compound is selected from the group consisting of polyurethane and polyurethane urea.

3. The medical tube of claim 1 wherein said size of the said cells or voids is $0.01\ d \leq 1 \leq 0.8\ d$.

* * * * *